(12) United States Patent
Schlom et al.

(10) Patent No.: US 7,598,225 B1
(45) Date of Patent: *Oct. 6, 2009

(54) GENERATION OF IMMUNE RESPONSE TO PROSTATE-SPECIFIC ANTIGEN (PSA)

(75) Inventors: Jeffrey Schlom, Potomac, MD (US); Dennis L. Panicali, Acton, MA (US)

(73) Assignee: The United States of America as represented by the Department of Health and Human Services, Bethesda, MD (US)

( * ) Notice: Subject to any disclaimer, the term of this patent is extended or adjusted under 35 U.S.C. 154(b) by 647 days.

This patent is subject to a terminal disclaimer.

(21) Appl. No.: 09/693,121

(22) Filed: Oct. 20, 2000

Related U.S. Application Data

(63) Continuation of application No. 08/500,306, filed on Jul. 10, 1995, now Pat. No. 6,165,460.

(51) Int. Cl.
  *A61K 48/00* (2006.01)
(52) U.S. Cl. .......... 514/44; 424/93.1
(58) Field of Classification Search .......... 536/23.1; 434/93.1, 93.21, 93.2, 93.6, 199.1; 435/235.1
See application file for complete search history.

(56) References Cited

U.S. PATENT DOCUMENTS

| 5,833,975 | A | * | 11/1998 | Paoletti et al. | |
| 5,925,362 | A | * | 7/1999 | Spitler et al. | |
| 6,165,460 | A | * | 12/2000 | Schlom et al. | 424/93.2 |

FOREIGN PATENT DOCUMENTS

| EP | 0 652 014 | A | 5/1995 |
| EP | 0 725 139 | A | 8/1996 |
| WO | WO 92/19266 | * | 11/1992 |
| WO | WO 95/04548 | * | 2/1995 |
| WO | WO 95 04548 | A | 2/1995 |

OTHER PUBLICATIONS

Fenton RG Journal of National Cancer Insititutes Aug. 18, 1993, 85 (16):1294-302.*
Montefiori et al J. Clin. Immunol Nov. 1992 12(6):429-439.*
Paoletti et al Ann N Y Acad Sci. Aug. 1993 12;690:292-300.*
Hodge et al (Cancer Res. Nov. 1994;54(21):5552-5).*
Fields et al (Fundamental Virology 2nd Ed. Raven Press 1991, pp. 953-973.*
Fields et al (Fields Virology 3rd Edition vol. 2, Lippincott, Williams, and Wilkins, pp. 2637-2671).*
Abulafia et al., Fed Am Soc Exp Bio., J4(7) 1990.
Corman et al., Journal of Urology, 155 (5 suppl.) 1996.
Correlae et al., Proc. Amer. Assoc. Can Res Annual Meeting 37 (0): 488-489 1996.
Hodge et al., International Journal of Cancer, 63(2): 231-237 1995.
Lu et al., Hybridoma 12(4): 381-9 1993.
Ross et al., Biotechnology Therapeutics 4 (3-4): 197-211, 1993.
Johnson et al., J. Virology vol. 68/5; pp. 3145-3153, 1994.
Montefiore et al., J. Clin. Immunology 12/6, pp. 429-439, 1992.
Graham et al., J. Infectious Diseases, vol. 66/2, pp. 244-252, 1992.
Cooney et al., Lancet, vol. 337/8741, pp. 267-272, 1991.

* cited by examiner

*Primary Examiner*—Christopher H Yaen
(74) *Attorney, Agent, or Firm*—Leydig, Voit & Mayer, Ltd.

(57) ABSTRACT

We have discovered that by using a recombinant viral vector, preferably a pox virus vector having at least one insertion site containing a DNA segment encoding prostate-specific antigen (PSA), operably linked to a promoter capable of expression in the host, a specific humoral and cellular immune response to PSA can be generated. The method preferably comprises introducing a sufficient amount of the recombinant pox virus vector into a host to stimulate the immune response, and contacting the host with additional PSA at periodic intervals thereafter. The additional PSA may be added by using a second pox virus vector from a different pox genus. In another embodiment, additional PSA can be added by contacting the host with PSA by a variety of other methods, including in one preferred embodiment adding PSA. The PSA may be formulated with an adjuvant or in a liposomal formulation.

18 Claims, 2 Drawing Sheets

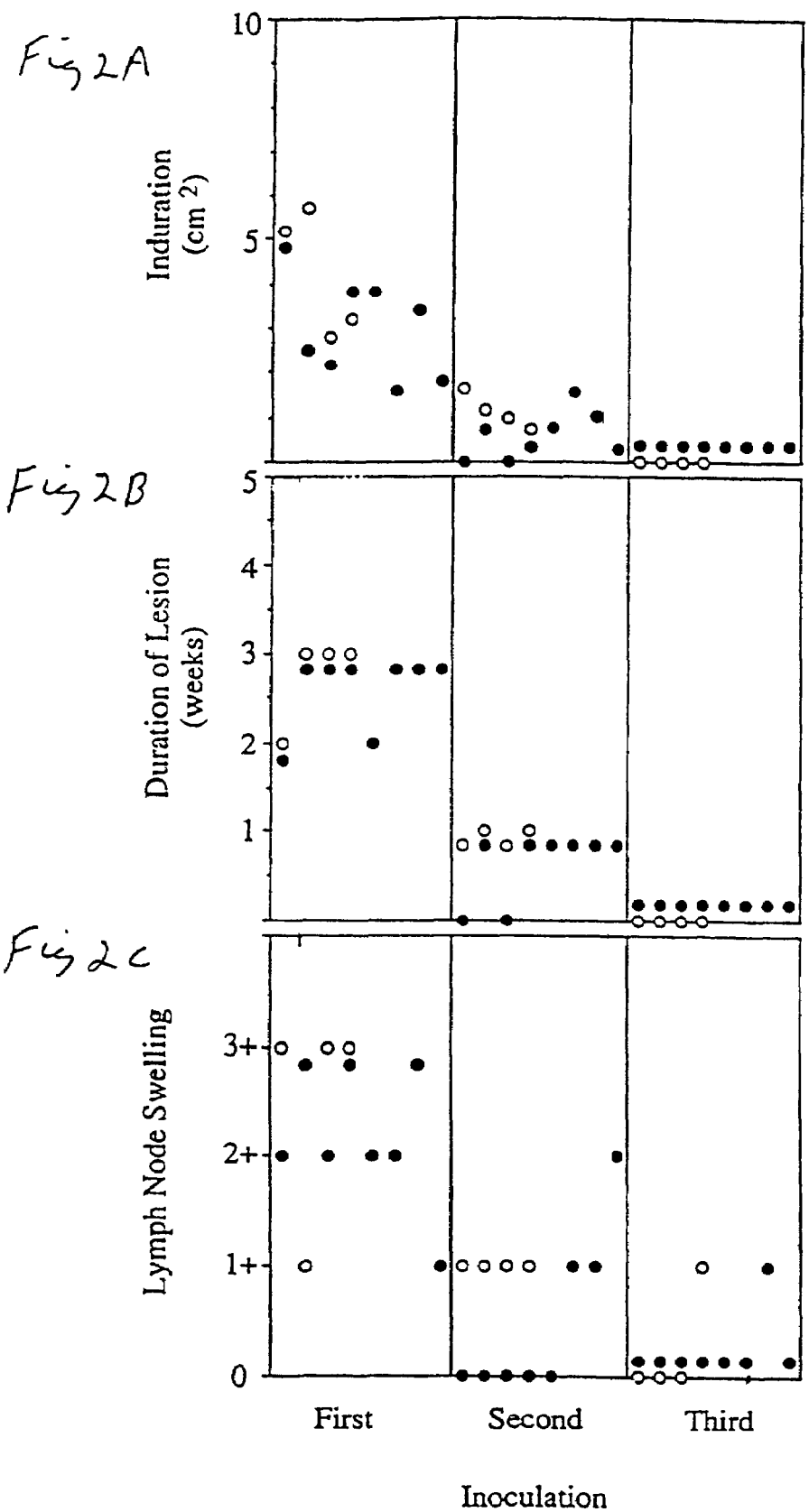

SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:

```
<223> OTHER INFORMATION: Synthetic Polynucleotide

<400> SEQUENCE: 1
tctagaagcc ccaagcttac cacctgca                                28

<210> SEQ ID NO 2
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 2
tctagatcag gggttggcca cgatggtgtc cttgatccac t                  41
```

GENERATION OF IMMUNE RESPONSE TO PROSTATE-SPECIFIC ANTIGEN (PSA)

RELATED APPLICATIONS

This application is a continuation of an application Ser. No. 08/500,306, filed Jul. 10, 1995, now U.S. Pat. No. 6,165,460.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 711 bytes ASCII (Text) file named "701319_ST25.txt," created on July 20, 2009.

FIELD OF THE INVENTION

The present invention relates generally to generation of cellular and humoral immune responses to a mammalian prostate-specific antigen (PSA).

BACKGROUND OF THE INVENTION

Cancer of the prostate is the most commonly diagnosed cancer in men and is the second most common cause of cancer death (Carter, et al., 1990; Armbruster, et al., 1993). If detected at an early stage, prostate cancer is potentially curable. However, a majority of cases are diagnosed at later stages when metastasis of the primary tumor has already occurred (Wang, et al., 1982). Even early diagnosis is problematic because not all individuals who test positive in these screens develop cancer. Present treatment for prostate cancer includes radical prostatectomy, radiation therapy, or hormonal therapy. No systemic therapy has clearly improved survival in cases of hormone refractory disease. With surgical intervention, complete eradication of the tumor is not always achieved and the observed re-occurrence of the cancer (12-68%) is dependent upon the initial clinical tumor stage (Zietman, et al., 1993). Thus, alternative methods of treatment including prophylaxis or prevention are desirable.

Prostate specific antigen (PSA) is a 240 amino acid member of the glandular kallikrein gene family. (Wang, et al., 1982; Wang, et al., 1979; Bilhartz, et al., 1991). PSA is a serine protease, produced by normal prostatic tissue, and secreted exclusively by the epithelial cells lining prostatic acini and ducts (Wang, et al., 1982; Wang, et al., 1979; Lilja, et al., 1993). Prostate specific antigen can be detected at low levels in the sera of healthy males without clinical evidence of prostate cancer. However, during neoplastic states, circulating levels of this antigen increase dramatically, correlating with the clinical stage of the disease (Schellhammer, et al., 1993; Huang, et al., 1993; Kleer, et al., 1993; Oesterling, et al., 1991). Prostate specific antigen is now the most widely used marker for prostate cancer. The tissue specificity of this antigen makes PSA a potential target antigen for active specific immunotherapy (Armbruster, et al., 1993; Brawer, et al., 1989), especially in patients who have undergone a radical prostatectomy in which the only PSA expressing tissue in the body should be in metastatic deposits. Recent studies using in-vitro immunization have shown the generation of CD4 and CD8 cells specific for PSA (Peace et al., 1994; Correale et al., 1995). However, although weak natural killer cell responses have been occasionally documented in prostate cancer patients (Choe, et al., 1987), attempts to generate an in vivo immune response have met with limited success. For example, several attempts to actively immunize patients with prostate adenocarcinoma cells admixed with *Bacillus* Calmette-Guerin (BCG) have shown little or no therapeutic benefit (Donovan, et al., 1990). The ability to elicit an immune response as a result of exposure to PSA in vivo would be extremely useful.

Vaccinia virus has been used in the world-wide eradication of smallpox. This virus has been shown to express a wide range of inserted genes, including several tumor associated genes such as p97, HER-2/neu, p53 and ETA (Paoletti, et al., 1993). Other pox viruses that have been suggested as useful for expression of multiple genes include avipox such as fowl pox. Cytokines expressed by recombinant vaccinia virus include IL-1, IL-2, IL-5, IL-6, TNF-α and IFN-γ (Paoletti, et al., 1993). Recombinant pox viruses, for example vaccinia viruses, are being considered for use in therapy of cancer because it has been shown in animal models that the co-presentation of a weak immunogen with the highly immunogenic poxvirus proteins can elicit a strong immune response against the inserted gene product (Kaufman, et al., 1991; Paoletti, et al., 1993; Kantor, et al., 1992a; Kantor, et al., 1992b; Irvine, et al., 1993; Moss, et al., 1993). A recombinant vaccinia virus containing the human carcinoembryonic antigen gene has just completed phase 1 clinical trials in carcinoma patients with no evidence of toxicity other than that observed with the wild type smallpox vaccine (Kantor, et al., 1992b).

Currently, models for the evaluation of prostate therapeutics include the canine (McEntee, et al., 1987), and the Dunning rat (Isaacs. et al., 1986); neither of these models, however, are practical for the study of PSA-recombinant vaccines due to the very low homology of rat and canine PSA to human PSA (Karr, et al., 1995; Schroder, et al., 1982). In contrast, the prostate gland of the rhesus monkey is structurally and functionally similar to the human prostate (Wakui, et al., 1992). At the molecular level, there is 94% homology between either the amino acid or nucleic acid sequences of rhesus PSA (Gauthier, et al., 1993) and those sequences of human prostate specific antigen (Karr, et al., 1995; Lundwall, et al., 1987). Thus, human PSA is essentially an autoantigen in the rhesus monkey. Accordingly, the rhesus monkey can serve as a model for autologous anti-PSA immune reactions.

SUMMARY OF THE INVENTION

We have discovered that by using a recombinant viral vector, preferably a pox virus vector having at least one insertion site containing a DNA segment encoding prostate-specific antigen (PSA), or a cytotoxic T-cell eliciting epitope thereof, operably linked to a promoter capable of expression in the host, a specific humoral and cellular immune response to PSA can be generated. The method preferably comprises introducing a sufficient amount of the recombinant pox virus vector into a host to stimulate the immune response, and contacting the host with additional PSA at periodic intervals thereafter. The additional PSA, or a cytotoxic T-cell eliciting epitope thereof, may be added by using a second pox virus vector from a different pox genus. In another embodiment, additional PSA can be added by contacting the host with PSA by a variety of other methods, including in one preferred embodiment adding PSA. The PSA may be formulated with an adjuvant or in a liposomal formulation.

In a further embodiment, an immune response to PSA can be generated by contacting the host initially with a sufficient amount of PSA, or a cytotoxic T-cell eliciting epitope thereof, to stimulate an immune response and at periodic intervals thereafter contacting the host with additional PSA. The additional PSA, or a cytotoxic T-cell generating fragment thereof, may be added using a pox virus vector as discussed above.

We have also discovered that human cytotoxic T-cells specific for PSA can be produced using a cytotoxic T-cell eliciting epitope of the PSA and that these cells have the ability to lyse PSA-expressing human prostate carcinoma cells.

As used herein the term "prostate specific antigen" includes the native protein whether purified from a native source or made by recombinant technology, as well as any polypeptide, mutein or portion derived therefrom that is capable of generating an immune response to a native conformationally correct PSA. For example, one can make conservative amino acid substitutions in the molecule without adversely affecting the ability to use the recombinant to generate an antibody that will also recognize native PSA.

The pox virus is preferably selected from the group of pox viruses consisting of suipox, avipox, capripox and orthopox virus. Preferred orthopox include vaccinia, rabbit pox and raccoon pox. Preferred avipox includes fowipox, canary pox and pigeon pox. A more preferred avipox is fowipox. The preferred suipox is swinepox.

Vaccinia viral vectors may elicit a strong antibody response. Thus while numerous boosts with vaccinia vectors are possible, its repeated use may not be preferred in certain instances. We have discovered that by using pox from different genera to boost, this sensitivity problem can be minimized. In accordance with the present invention, in order to avoid such problems, preferably, when the first or initial pox virus vector is vaccinia, the second and subsequent pox virus vectors are selected from the pox viruses from a different genus such as suipox, avipox, capripox or an orthopox immunogenically distinct from vaccinia.

Adjuvants include, for example, RIBI Detox, QS21, and incomplete Freund's adjuvant. Liposomal formulations can also be used.

Human cytotoxic T-cells specific for PSA produced in accordance with the present invention can be isolated from a human host. These cells can be used in drug assays, used to map cytotoxic T-cells eliciting antigen epitopes or in adoptive cell therapy.

BRIEF DESCRIPTION OF THE DRAWINGS

FIGS. 2A, 2B and 2C show the manifestation of rV-PSA immunization. In FIG. 2A, the area of lesions was measured 7 days following each inoculation of rhesus monkeys with either V-Wyeth (open circles) or rV-PSA (closed circles). In FIG. 2B, the duration of the lesion was monitored as time of scab disappearance. In FIG. 2C, the extent of lymph node swelling was recorded and characterized as very swollen (3+), i.e., more than two axillary nodes swollen; swollen (2+), i.e., one or two nodes easily palpable; marginally swollen (1+), i.e., one node was barely palpable; or not swollen (0), 7 days following inoculation with vaccinia virus. Each symbol represents one monkey.

DETAILED DESCRIPTION OF THE INVENTION

Figure 1:
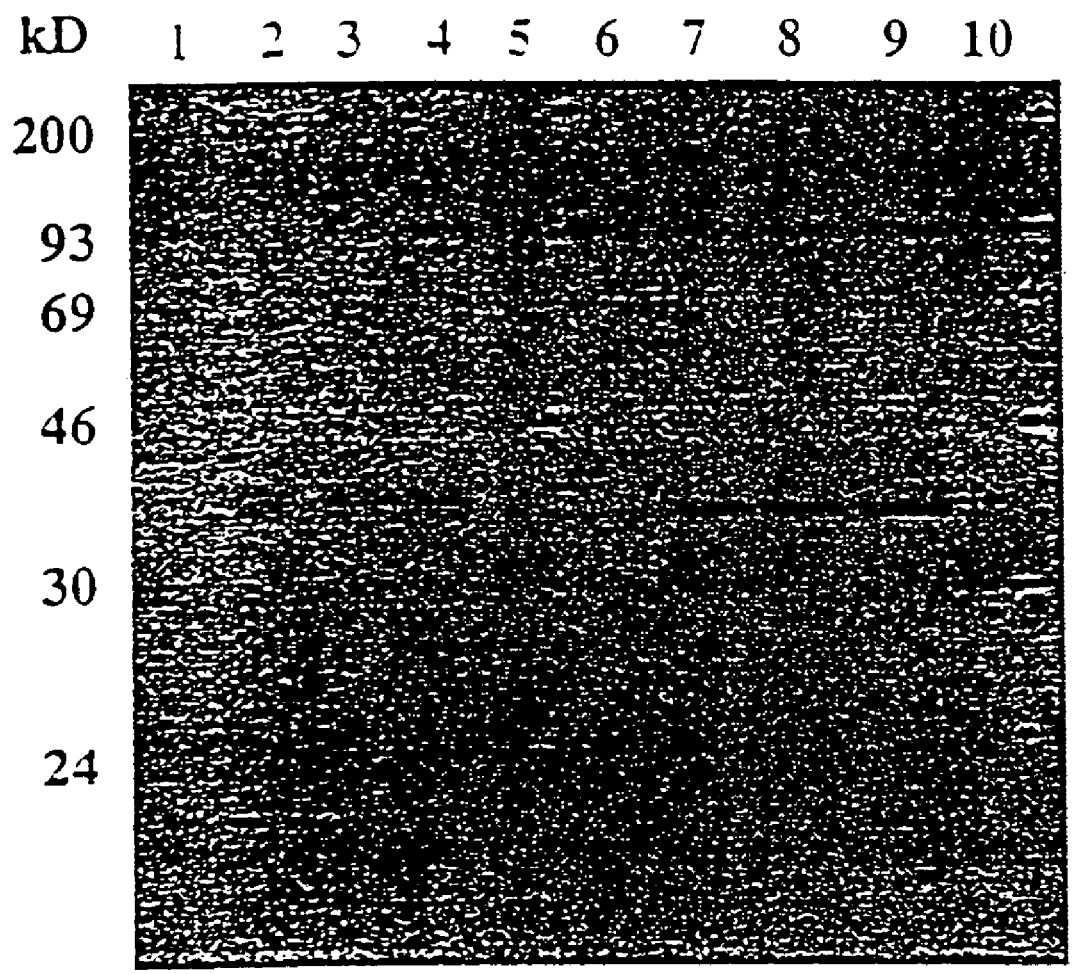
FIG. 1 shows a Western blot of PSA from rV-PSA infected BSC-40 cells. Lanes 2-4 are extracts from supernatant fluid from cells infected overnight with rV-PSA at an MOI of 1, while Lanes 7-9 are extracts from the corresponding infected cells. Lanes 1 and 7 are supernatant extracts and cell extracts from V-Wyeth infected cells. Blot was developed using a specific MAb for human PSA. This blot illustrates that cells infected with rV-PSA authentically express and secrete the 33 kD PSA protein.

We have induced an immune response specific to PSA in the rhesus monkey model by placing the PSA gene into a recombinant viral vector, i.e, a pox vector such as vaccinia virus.

Additionally, an immune response to PSA can be generated by contacting the host initially with a sufficient amount of PSA, or a cytotoxic T-cell eliciting epitope thereof, to stimulate an immune response and at periodic intervals thereafter contacting the host with additional PSA. The additional PSA, or a cytotoxic T-cell generating fragment thereof, may be added using a pox virus vector.

A DNA fragment encoding the open reading frame of human PSA can be obtained, for example, from total RNA extracted from the human metastatic prostate adenocarcinoma cell line, LNCaP.FGC (CRL 1740, American Type Cell Culture (ATCC), Rockville, Md.) by reverse transcriptase PCR using PSA specific oligonucleotide primers 5' TCTA-GAAGCCCCAAGCTTACCACCTGCA 3' (SEQ. ID. NO.: 1), 5' TCTAGATCAGGGGTTGGCCACGATGGT-GTCCTTGATCCACT 3' (SEQ. ID. NO.:2). The nucleotide sequence of the PSA cDNA has been published (Lundwall, et al., 1987).

Recombinant human PSA can be obtaining using a baculovirus expression system in accordance with the method of Bei et al., *J. Clin. Lab. Anal.*, 9:261-268 (1995), the disclosure of which is herein incorporated by reference.

Viral Vector

Basic techniques for preparing recombinant DNA viruses containing a heterologous DNA sequence encoding the carcinoma self-associated antigen or cytotoxic T-cell eliciting epitope are known to the skilled artisan and involve, for example, homologous recombination between the viral DNA sequences flanking the DNA sequence in a donor plasmid and homologous sequences present in the parental virus (Mackett, et al., *Proc. Natl. Acad. Sci. USA* 79:7415-7419 (1982)). For example, recombinant viral vectors such as a pox viral vector can be used in delivering the gene. The vector can be constructed for example by steps known in the art, e.g. analogous to the methods for creating synthetic recombinants of the fowlpox virus described in U.S. Pat. No. 5,093,258, the disclosure of which is incorporated herein by reference. Other techniques include using a unique restriction endonuclease site that is naturally present or artificially inserted in the parental viral vector to insert the heterologous DNA.

Pox viruses useful in practicing the present invention include orthopox, suipox, avipox and capripox virus.

Orthopox include vaccinia, ectromelia and raccoon pox. The preferred orthopox is vaccinia.

Avipox includes fowipox, canary pox and pigeon pox. The preferred avipox is fowipox.

Capripox include goatpox and sheeppox.

A preferred suipox is swinepox.

Other viral vectors that can be used include other DNA viruses such as herpes virus and adenoviruses, and RNA viruses such as retroviruses and polio.

For example, the DNA gene sequence to be inserted into the virus can be placed into a donor plasmid, e.g., an *E. coli* plasmid construct, into which DNA homologous to a section of DNA such as that of the insertion site of the poxvirus where the DNA is to be inserted has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA which is the desired insertion region. With a parental pox viral vector, a pox promoter is used. The resulting plasmid construct is then amplified by growth within *E. coli* bacteria and isolated. Preferably, the plasmid also contains an origin of replication such as the *E. coli* origin of replication, and a marker such as an antibiotic resistance gene for selection and propagation in *E. coli*.

Second, the isolated plasmid containing the DNA gene sequence to be inserted is transfected into a cell culture, e.g., chick embryo fibroblasts, along with the parental virus, e.g., poxvirus. Recombination between homologous pox DNA in the plasmid and the viral genome respectively results in a recombinant poxvirus modified by the presence of the promoter-gene construct in its genome, at a site which does not affect virus viability.

As noted above, the gene is inserted into a region (insertion region), in the virus which does not affect virus viability of the resultant recombinant virus. The skilled artisan can readily identify such regions in a virus by, for example, randomly testing segments of virus DNA for regions that allow recombinant formation without seriously affecting virus viability of the recombinant. One region that can readily be used and is present in many viruses is the thymidine kinase (TK) gene. For example, the TK gene has been found in all pox virus genomes examined [leporipoxvirus: Upton, et al., *J. Virology*, 60:920 (1986) (shope fibroma virus); capripoxvirus: Gershon, et al., *J. Gen. Virol.*, 70:525 (1989) (Kenya sheep-1); orthopoxvirus: Weir, et al., *J. Virol.*, 46:530 (1983) (vaccinia); Esposito, et al., *Virology*, 135:561 (1984) (monkeypox and variola virus); Hruby, et al., *PNAS*, 80:3411 (1983) (vaccinia); Kilpatrick, et al., *Virology*, 143:399 (1985) (Yaba monkey tumor virus); avipoxvirus: Binns, et al., *J. Gen. Virol.* 69:1275 (1988) (fowlpox); Boyle, et al., *Virology*, 156:355 (1987) (fowlpox); Schnitzlein, et al., *J. Virological Methods*, 20:341 (1988) (fowipox, quailpox); entomopox (Lytvyn, et al., *J. Gen. Virol.* 73:3235-3240 (1992)].

In vaccinia, in addition to the TK region, other insertion regions include, for example, the HindIII M fragment.

In fowipox, in addition to the TK region, other insertion regions include, for example, the BamHI J fragment [Jenkins, et al., *AIDS Research and Human Retroviruses* 7:991-998 (1991)] the EcoRI-HindIII fragment, EcoRV-HindIII fragment, BamHI fragment and the HindIII fragment set forth in EPO Application No. 0 308 220 A1. [Calvert, et al., *J. of Virol.* 67:3069-3076 (1993); Taylor, et al., *Vaccine* 6:497-503 (1988); Spehner, et al., (1990) and Boursnell, et al., *J. of Gen. Virol.* 71:621-628 (1990)].

In swinepox preferred insertion sites include the thymidine kinase gene region.

In addition to the requirement that the gene be inserted into an insertion region, successful expression of the inserted gene by the modified poxvirus requires the presence of a promoter operably linked to the desired gene, i.e., in the proper relationship to the inserted gene. The promoter must be placed so that it is located upstream from the gene to be expressed. Promoters are well known in the art and can readily be selected depending on the host and the cell type you wish to target. For example in poxviruses, pox viral promoters should be used, such as the vaccinia 7.5K, 40K or fowlpox promoters such as FPV C1A. Enhancer elements can also be used in combination to increase the level of expression. Furthermore, the use of inducible promoters, which are also well known in the art, in some embodiments are preferred.

A specific immune response for PSA can be generated by administering between about $10^5$-$10^9$ pfu of the recombinant pox virus, constructed as discussed above to a host, more preferably one uses $10^7$ pfu. The preferred host is a human. At least one interval thereafter, which is preferably one to three months later, the immune response is boosted by administering additional antigen to the host. More preferably there is at least a second "boost" preferably one to three months after the first boost. The antigen may be administered using the same pox virus vector. The antigen may preferably be administered using a second pox virus vector from a different pox genera, or may be administered directly using, for example, an adjuvant or liposome. Cytokines, e.g., IL-2, IL-6, IL-12 or co-stimulatory molecules, e.g., B7.1, B7.2, may be used as biologic adjuvants and can be administered systemically to the host or co-administered via insertion of the genes encoding the molecules into the recombinant pox vector.

Adjuvants include, for example, RIBI Detox (Ribi Immunochemical), QS21 and incomplete Freund's adjuvant.

Generation of Cytotoxic T-Cells

Cytotoxic T-cells specific for PSA can be established from peripheral blood mononuclear cells (PBMC) obtained from a host immunized as discussed above. For example, PBMC can be separated by using Lymphocyte Separation Medium gradient (Organon Teknika, Durham, N.C., USA) as previously described [Boyum, et al., *Scand J. Clin Lab Invest* 21: 77-80 (1968)]. Washed PBMC are resuspended in a complete medium, for example, RPMI 1640 (GIBCO) supplemented with 10% pool human AB serum (Pel-Freeze Clinical System, Brown Dear, Wis., USA), 2 mM glutamine, 100 U/ml penicillin and 100 µg/ml of streptomycin (GIBCO). PBMC at a concentration of about $2\times10^5$ cells in complete medium in a volume of, for example, 100 µl are added into each well of a 96-well flat-bottom assay plate (Costar, Cambridge, Mass., USA). The antigen or peptides are added into the cultures in a final concentration of about 50 µg/ml and incubated at 37° c. in a humidified atmosphere containing 5% $CO_2$ for 5 days. After removal of peptide containing media, the cultures are provided with fresh human IL-2 (10 U/ml) after 5 days and replenished with IL-2 containing medium every 3 days. Primary cultures are restimulated with the same peptide (50 µg/ml) on day 16. $5\times10^5$ irradiated (4,000 rad) autologous PBMC are added in a volume of about 50 µl complete medium as antigen-presenting cells (APC). About five days later, the cultures are provided with human IL-2 containing medium as described previously. Cells are restimulated for 5 days at intervals of 16 days.

Epitope Mapping

The cytotoxic T-cells of the present invention can be used to determine the epitope of the PSA that elicits a cytoxic T-cell. For example, one can cut the PSA into numerous peptide fragments. Alternatively, the fragments can be chemically synthesized. Cytotoxic T-cells can then be plated and different fragments added to different wells. Only T-cells which recognize one of the pre-selected peptide fragments as an epitope will continue to expand, thereby permitting ready identification.

These fragments can then be used to elicit cytotoxic T-cell instead of using the whole protein. Additionally, one can prepare other fragments containing the epitope to enhance its ability to elicit a cytoxic T-cell response. Modifications to these fragments are well known in the art and include the use of conjugates, specific amino acid residues such as cystines, etc.

Drug Assay

The cytotoxic T-cell can also be used to screen for compounds which enhance the ability of the antigen to create a cytotoxic T-cell response. For example, cytotoxic T-cells can be incubated with a selected epitope, for example, in a microtiter plate. The compound to be tested, e.g. a drug, is then added to the well and the growth of the T-cells is measured. T-cell expansion indicates that the test compound enhances the T-cell response. Such compounds can be further evaluated.

Therapy

The cytotoxic T-cell can be cultured to amplify its number and then injected back into the host by a variety of means. Generally, between $1 \times 10^5$ and $2 \times 10^{11}$ cytotoxic T-cells per infusion are administered in, for example, one to three infusions of 200 to 250 ml each over a period of 30 to 60 minutes. After the completion of the infusions, the patient may be treated with recombinant interleukin-2 with a dose of 720,000 IU per kilogram of body weight intravenously every eight hours; some doses can be omitted depending on the patient's tolerance for the drug. In addition, after infusion, additional antigen or fragments containing T-cell eliciting epitope(s) may be administered to the patient to further expand the T-cell number. The antigen or epitope may be formulated with an adjuvant and/or may be in a liposomal formulation.

The cytotoxic T-cells can also be modified by introduction of a viral vector containing a DNA encoding TNF and reintroduced into a host in an effort to enhance the anti-tumor activity of the cells. Other cytokines can also be used.

The recombinant vector can be administered using any acceptable route, including, for example, scarification and injection, e.g., intradermal, subcutaneous, intramuscular, intravenous or intraperitoneal.

For parenteral administration, the recombinant vectors will typically be injected in a sterile aqueous or non-aqueous solution, suspension or emulsion in association with a pharmaceutically-acceptable carrier such as physiological saline.

REFERENCE EXAMPLE 1

Construction of Vectors

Pox Viruses

A number of pox viruses have been developed as live viral vectors for the expression of heterologous proteins (Cepko et al., *Cell* 37:1053-1062 (1984); Morin et al., *Proc. Natl. Acad. Sci. USA* 84:4626-4630 (1987); Lowe et al., *Proc. Natl. Acad. Sci. USA*, 84:3896-3900 (1987); Panicali & Paoletti, *Proc. Natl. Acad. Sci. USA*, 79:4927-4931 (1982); Mackett et al., *Proc. Natl. Acad. Sci. USA*, 79:7415-7419 (1982)). Representative fowlpox and swinepox virus are available through the ATCC under accession numbers VR-229 and VR-363, respectively.

DNA Vectors for In Vivo Recombination with a Parent Virus

Genes that code for desired carcinoma associated antigens are inserted into the genome of a pox virus in such a manner as to allow them to be expressed by that virus along with the expression of the normal complement of parent virus proteins. This can be accomplished by first constructing a DNA donor vector for in vivo recombination with a pox virus.

In general, the DNA donor vector contains the following elements:

(i) a prokaryotic origin of replication, so that the vector may be amplified in a prokaryotic host;

(ii) a gene encoding a marker which allows selection of prokaryotic host cells that contain the vector (e.g., a gene encoding antibiotic resistance);

(iii) at least one gene encoding a desired protein located adjacent to a transcriptional promoter capable of directing the expression of the gene; and (iv) DNA sequences homologous to the region of the parent virus genome where the foreign gene(s) will be inserted, flanking the construct of element (iii).

Methods for constructing donor plasmids for the introduction of multiple foreign genes into pox virus are described in WO91/19803, the techniques of which are incorporated herein by reference. In general, all DNA fragments for construction of the donor vector, including fragments containing transcriptional promoters and fragments containing sequences homologous to the region of the parent virus genome into which foreign genes are to be inserted, can be obtained from genomic DNA or cloned DNA fragments. The donor plasmids can be mono-, di-, or multivalent (i.e., can contain one or more inserted foreign gene sequences).

The donor vector preferably contains an additional gene which encodes a marker which will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., *J. Virol.*, 62:1046 (1988); Falkner and Moss., *J. Virol.*, 62:1849 (1988); Franke et al., *Mol. Cell. Biol.*, 5:1918 (1985), as well as genes such as the *E. coli* lacZ gene, that permit identification of recombinant viral plaques by calorimetric assay (Panicali et al., *Gene*, 47:193-199 (1986)).

Integration of Foreign DNA Sequences into The Viral Genome and Isolation of Recombinants Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (Panicali and Paoletti, U.S. Pat. No. 4,603,112, WO89/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK$^-$ and can be selected on this basis (Mackett et al., *Proc. Natl. Acad. Sci. USA*, 79:7415 (1982)). Alternatively, co-integration of a gene encoding a marker or indicator gene with the foreign gene(s) of interest, as described above, can be used to identify recombinant progeny. One preferred indicator gene is the *E. coli* lacZ gene: recombinant viruses expressing β-galactosidase can be selected using a chromogenic substrate for the enzyme (Panicali et al., *Gene*, 47:193 (1986)).

Characterizing the Viral Antigens Expressed by Recombinant Viruses

Once a recombinant virus has been identified, a variety of methods can be used to assay the expression of the polypeptide encoded by the inserted gene. These methods include black plaque assay (an in situ enzyme immunoassay performed on viral plaques), Western blot analysis, radioimmunoprecipitation (RIPA), and enzyme immunoassay (EIA).

EXAMPLE 1

Generation of PSA Specific Immune Response

Materials and Methods

Recombinant Vaccinia Virus

A 786 bp DNA fragment encoding the entire open reading frame of human prostate specific antigen was amplified by reverse transcriptase PCR (GeneAmp RNA PCR Kit, Perkin Elmer, Norwalk, Conn.) from total RNA extracted from the human metastatic prostate adenocarcinoma cell line, LNCaP.FGC (CRL 1740, American Type Culture Collection (ATCC), Rockville, Md.). The predicted amino acid sequence derived from the PSA coding sequence was shown to be nearly identical to the published sequence (Lundwall, et al., 1987), differing only in a change from asparagine to tyrosine at position 220. The PSA DNA fragment, containing the entire coding sequence for PSA, 41 nucleotides of the 5' untranslated region, and 520 nucleotides of the 3' untranslated region, was inserted into the Xba I restriction endonuclease cleavage site of the vaccinia virus transfer vector pT116. The resulting plasmid, designated pT1001, contains the PSA gene under the control of the vaccinia virus 40K promoter (Gritz, et al. 1990) and the *E. coli* lacZ gene under the control of the fowlpox virus C1 promoter (Jenkins, et al., 1991). The foreign genes are flanked by DNA sequences from the Hind III M region of the vaccinia genome. A plaque-purified isolate from the Wyeth (New York City Board of Health) strain of vaccinia was used as the parental virus in the construction of the recombinant vaccinia virus. The generation of recombinant vaccinia virus was accomplished via homologous recombination between vaccinia sequences in the Wyeth vaccinia genome and the corresponding sequences in pT1001 in vaccinia-infected $RK_{13}$ cells (CCL 37, ATCC) transfected with pT1001. Recombinant virus was identified using a chromogenic assay, performed on viral plaques in situ, that detects expression of the lacZ gene product in the presence of halogenated indolyl-beta-D-galactoside (Bluo-gal), as described previously (Panacali, et al., 1986). Appropriate blue recombinant viruses were purified by Four rounds of plaque-purification. Virus stocks were prepared by clarifying infected $RK_{13}$ cell lysates followed by centrifugation through a 36% sucrose cushion.

Characterization of Recombinant Virus

Southern Analysis of DNA Recombination

The recombinant vaccinia genome was analyzed by viral DNA extraction, restriction endonuclease digestion with Hind III, and Southern blotting as previously described (Kaufman et al., 1991).

Western Analysis of Protein Expression

Confluent BSC-40 cells were infected with either parental wild type vaccinia virus (designated V-Wyeth) or recombinant vaccinia-PSA (designated rV-PSA) at an MOI of 1 in Dulbecco's Modified Eagle's Medium containing 2% fetal bovine serum. After an overnight infection, the medium was removed from the cells, and an aliquot was methanol precipitated to assay for the presence of secreted PSA. The infected cells were lysed in hypotonic lysis buffer (150 mM NaCl, 0.05% EDTA, 10 mM KCl, 1 mM PMSF) and then sonicated. Cell lysates and culture media were electrophoresed on an SDS-10% acrylamide gel. The proteins were transblotted to nitrocellulose, and the blot was incubated with a rabbit antibody specific for PSA (P0798, Sigma Chemical Co., St. Louis, Mo.) for 4 hours at ambient temperature, washed, and then incubated with goat anti-rabbit phosphatase-labeled secondary antibody (AP, Kirkegaard & Perry Laboratories, Gaithersburg, Md.) and developed according to the manufacture's instructions.

Generation of B-Cell Lines

Monkey autologous B lymphoblastoid cell lines (BLCL) were established by infecting $1\times10^5$ freshly isolated PBMCs in 100 ml of RPMI 1640 supplemented with L-glutamine, gentamicin, and 10% FCS (Biofluids, Rockville, Md.) with 100 ml supernatant from S594 cells (kindly provided by Dr. M. D. Miller, Harvard Medical School, New England Regional Primate Research Center, Southborough, Mass.), which contains the baboon herpesvirus *Herpes papio*, in a 96 well, flat-bottomed plate (Costar, Cambridge, Mass.). Following transformation, cells were expanded, and media changed once weekly.

Immunization of Monkeys

Twelve juvenile male rhesus monkeys (*Macaca mulatta*), ages 1 to 2 years, were assigned to three vaccination groups of four animals each. One animal from each group was prostatectomized. Animals were immunized 3 times on days 1, 29, and 57. Doses of either $1\times10^7$ or $1\times10^8$ PFU of rV-PSA were administered to 4 animals by skin scarification. V-Wyeth ($1\times10^8$ PFU) was administered to 4 animals as controls. The animals were housed and maintained at the Toxicology Research Laboratory, University of Illinois at Chicago (TRL/UIC) in accordance with the guidelines of the National Cancer Institute Animal Care and Use Committee and the Guide for the Care and Use of Laboratory Animals (Department of Health and Human Services Publication NIH 85-23, revised 1985 by the FDA Center for Biologics Evaluation and Research Office of Biological Product Review, Division of Product Quality Control, Pathology and Primatology Laboratory, Bethesda, Md.).

Toxicology

Physical examinations were performed on ketamine (Ketamine® HCl, 10 mg/kg I.M.) sedated animals. Rectal temperatures and weights were recorded for each monkey on a weekly basis. The vaccination site was observed and erythema and swelling were measured by caliper. Each animal was examined for regional lymphadenopathy, hepatomegaly, and splenomegaly. Any other gross abnormalities were also recorded.

Blood was obtained by venipuncture from the femoral vein of ketamine sedated animals before and after each immunization. A complete blood count, differential, hepatic and renal chemistry evaluation was performed on each monkey by TRL/UIC. Results were compared to normal primate values (Kantor et al., 1992b). Circulating levels of PSA before and after immunization were analyzed by radioimmunoassay (Tandem™, Hybritech, San Diego, Calif.).

Measurement of Antibody Titers

Prior to each immunization and 2 weeks following each immunization, anti-PSA antibody was quantified by ELISA. Microtiter plates were coated with purified PSA (100 ng/well, Calbiochem, La Jolla, Calif.), ovalbumin (100 ng/well, Sigma), or $1\times10^7$ PFU/well UV-inactivated V-Wyeth in PBS. The plates were blocked with 2% BSA in PBS, dried, and stored at −20° C. until used. The plates were incubated with serum diluted 1:5, as well as a monoclonal antibody for PSA (DAKO M750, Denmark) as a standard control, for 24 hours at 4° C. Plates were washed several times with PBS containing 1% BSA, and incubated at 37° C. for 45 min with horseradish peroxidase-conjugated goat anti-human IgG or IgM heavy chain specific antiserum (1:8000) (Southern Biotechnology Associates, Birmingham, Ala.) and antibody detected by HRP substrate system (Kirkegaard & Perry Laboratories, Gaithersburg, Md.) according to the manufacture's instructions. The absorbance of each well was read at 405 nm using a Bio-Tek EL310 microplate ELISA reader (Winooski, Vt.).

Lymphoproliferative Assay

Autologous monkey BLCL were plated at a density of $3\times10^6$ cells/well in 24 well plates with 160 mg/well purified PSA (Fitzgerald, Concord, Mass.) or 160 mg/well ovalbumin (Sigma) at 37° C. for 24 hours. Cells were then γ-irradiated (14000 rad), harvested, washed and suspended at a final concentration of $1\times10^7$/ml. Fresh monkey PBMCs from heparinized blood, 6 weeks to 7 months after the last immunization, were isolated on lymphocyte separation medium (Organon Teknika, West Chester, Pa.). Lymphoproliferative responses were evaluated by co-culturing $1.5\times10^5$ cells with $5\times10^5$ cells/well of autologous BLCL in 0.2 ml of RPMI 1640 supplemented with 10% heat-inactivated fetal calf serum in flat-bottomed 96 well plates (Costar) for 5 days. PBMCs were cultured with $2\times10^7$ PFU/ml UV-inactivated V-Wyeth as a recall antigen or 2 mg/ml Con-A as positive controls. Cells were labeled for the final 12-18 h of the incubation with 1 mCi/well [$^3$H]thymidine (New England Nuclear, Wilmington, Del.) and harvested with a PHD cell harvester (Cambridge Technology, Cambridge, Mass.). The incorporated radioactivity was measured by liquid scintillation counting (LS 6000IC; Beckman, Duarte, Calif.). The results from triplicate wells were averaged and are reported as mean±SEM.

Results

Generation and Characterization of Recombinant Virus

The cDNA fragment encoding the open reading frame of human PSA was obtained by reverse transcriptase PCR using PSA specific oligonucleotide primers 5' TCTAGAAGC-CCCAAGCTTACCACCTGCA 3' (SEQ. ID. NO.:1), 5' TCTAGATCAGGGGTTGGCCACGATGGT-GTCCTTGATCCACT 3' (SEQ. ID. NO.:2), and ligated into the vaccinia virus transfer vector pT106. This vector contains a strong vaccinia virus early/late promoter (designated P40) upstream of the multiple cloning site to drive the synthesis of the inserted gene product. The ligation and orientation of the PSA DNA fragment, as well as promoter position were verified by PCR and sequencing. The chimeric vector construct was inserted into the vaccinia virus genome Hind III M site by homologous recombination as previously reported (Kaufman, et al., (1991)), and confirmed by Southern analysis probing with $^{32}$P radiolabeled DNA corresponding to PSA sequences and vaccinia sequences in the Hind III M region (data not shown). The entire cDNA sequence of PSA in the vaccinia virus clone was shown to be nearly identical to the published sequences (Lundwall, et al., 1987).

Expression of recombinant protein was confirmed by western blot analysis of supernatant fluids and protein extracts from rV-PSA infected BSC-40 cells. These cells are routinely used for the evaluation of recombinant vaccinia products (Moss, et al., 1993). Incubation of cell supernatant blots from rV-PSA infected cells with rabbit anti-PSA antibody revealed a single immunoreactive polypeptide of approximately 33,000 daltons (FIG. 1, lanes 2-4). Similarly, incubation of protein extract blots from rV-PSA infected cells revealed a single band of the same molecular weight (FIG. 1, lanes 7-9). This is consistent with the predicted size of the PSA molecule (Armbruster, et al., 1993; Wang, et al., 1982). Cell supernatant blots (lane 1) or protein extract blots (lane 6) from cells infected with parental strain V-Wyeth remained negative for expression of PSA. These results thus demonstrate that a recombinant vaccinia virus can faithfully express the human PSA gene product.

Rhesus Monkey Model

The prostate gland of the rhesus monkey is structurally and functionally similar to the human prostate (Wakui, et al., 1992). At the molecular level, there is 94% homology between both the amino acid and nucleic acid sequences of rhesus PSA (Gauthier, et al., 1993) and human prostate specific antigen (Karr, et al., 1995; Lundwall, et al., 1987). Human PSA is essentially an autoantigen in the rhesus monkey.

Experimental Design

Table 1 delineates the protocol used in the immunization of 12 rhesus monkeys with either rV-PSA or the control V-Wyeth by skin scarification. Three groups of 4 animals were immunized with either rV-PSA at $1\times10^7$ PFU/dose, rV-PSA at $1\times10^8$ PFU/dose, or V-Wyeth at $10^8$ PFU/dose 3 times at 4 week intervals. These doses were chosen to ascertain the maximum tolerated dose for safety as well as to obtain maximum humoral and cell-mediated responses to PSA.

The rhesus monkeys were divided into 3 groups: high dose V-Wyeth, low dose rV-PSA, and high dose rV-PSA. One animal in each group was surgically prostatectomized to parallel two situations with regard to potential therapy in humans: (a) prostate intact, with primary and/or metastatic disease; or (b) patients prostatectomized with prostate cancer metastatic deposits. The presence of an intact prostate gland could conceivably serve as an antigen 'sink', either inducing anergy through persistence of antigen, or masking immunological effects by sequestering reactive cells or antibodies.

Physical Consequence of Immunization

The area of the lesions induced by rV-PSA or V-Wyeth was analyzed 7 days following each inoculation. In general, more induration was seen after the first inoculation, compared to the second inoculation (FIG. 2A). After the third inoculation, there was no swelling of the vaccination site. The duration of the lesion following each immunization was shorter after each inoculation (FIG. 2B). Regional lymph node swelling following vaccination was greater in most monkeys following the first immunization, compared to the second, or third immunization (FIG. 2C). In general, no differences were seen in these parameters with the use of rV-PSA or V-Wyeth. Monkeys receiving V-Wyeth were compared with those receiving rV-PSA with respect to constitutional symptoms. Mild temperature elevations were seen in all animals following vaccination. There was no evidence of weight loss, hepatomegaly or splenomegaly in any of the animals, and there was no differences between V-Wyeth or rV-PSA treated animals (data not shown). Animals were tested for complete blood count, differential, and hepatic and renal chemistries. Complete blood counts remained within normal limits throughout the study in both V-Wyeth and rV-PSA immunized animals (Table 2). Hepatic and renal functions were assessed prior to immunization and 12 weeks following primary immunization (Table 3). Parameters analyzed included alkaline phosphatase, blood urea nitrogen, alanine aminotransferase, aspartate aminotransferase, lactate dehydrogenase, and creatine and creatine kinase levels. There was no significant difference between animals receiving V-Wyeth or rV-PSA. There was no detectable PSA in the circulation of any of these monkeys after any immunization (detection limit was 0.1 ng/ml). At this time, which is 54 weeks post all immunizations, no toxicities were observed in monkeys of any of the groups, including those which were prostatectomized.

PSA Specific Humoral Responses

As indicated in Table 1, monkeys 1-4 were administered V-Wyeth while monkeys 5-12 were administered rV-PSA. Sera from each of these monkeys were analyzed by ELISA for immunoreactivity to PSA or UV-inactivated V-Wyeth, and ovalbumin as control antigen. Sera obtained from monkeys prior to vaccination were negative for reactivity to PSA (Table 4, PI). Fifteen days following primary immunization, monkeys in both the $1 \times 10^8$ and $1 \times 10^7$ dose rV-PSA groups developed low titer IgM antibodies specific for PSA (titers were determined at a 1:5 serum dilution). Although other isotypes of antibody were analyzed (IgG, IgA, IgM), only IgM was induced by rV-PSA throughout the observation period of 270 days. The antibody titers decreased over the 4 weeks prior to the next inoculation. Prior to the second vaccination on day 29, 3 of 4 animals in the $1 \times 10^7$ rV-PSA group remained positive for PSA antibody, while 4 of 4 animals remained positive in the $1 \times 10^8$ rV-PSA group. Anti-PSA antibody titers increased after the second vaccination on day 29, but remained static after the third vaccination on day 57. By 270 days after the primary immunization, all animals were negative for PSA IgM antibody. Monkeys remained negative for IgG specific for PSA throughout the observation period (data nor shown). There was no correlation between rV-PSA dose and anti-PSA IgM titer, nor was there any apparent effect of prostatectomy. All monkey sera were negative for IgG or IgM to ovalbumin at all time points; as a positive control, however, the IgG titer in all three treatment groups to vaccinia virus was greater than 1:2000 as early as 29 days after the primary immunization (data not shown).

In general, vaccinia virus is a weak human pathogen (Paoletti et al., 1993). Following vaccination, local erythema, induration, low-grade fever, and regional lymphadenopathy are common. The virus replicates in the epidermal cells of the skin and the virus is usually cleared within 14 days. All monkeys, whether given V-Wyeth or rV-PSA, exhibited the usual low grade constitutional symptoms of a vaccinia virus infection (FIG. 2). There was no evidence of any adverse effects as indicated by changes in blood counts, differentials, hepatic and renal chemistries (Tables 2-3). The monkeys appeared healthy, without any physical signs of toxicity, throughout the 54 weeks of observation.

Although the rV-PSA construct was unable to elicit an anti-PSA IgG response, PSA specific IgM responses were noted in all rV-PSA immunized monkeys regardless of dose level (Table 4). These antibody responses were of low titer, short lived and could not be boosted, indicating induction of a primary response but not memory B-cells or affinity maturation.

PSA Specific Lymphoproliferative Assay

PSA specific T-cell responses in monkeys immunized with rV-PSA or V-Wyeth were analyzed using a lymphoproliferative assay. As seen in Table 5, the PBMCs from all monkeys analyzed responded, regardless of whether they received rV-PSA or V-Wyeth, to the lymphocyte mitogen concanavalin-A, as well as with the recall antigen UV-inactivated V-Wyeth. Differential responses to PSA versus medium alone or ovalbumin were seen in 1 animal (number 6) in the $1 \times 10^7$ PFU rV-PSA group. All PBMCs from animals in the $1 \times 10^8$ PFU rV-PSA group, however, responded to PSA in this assay. This experiment was repeated 5 times with similar results and data shown in Table 5 is from PBMCs isolated from monkeys 270 days after the primary immunization. No differences in PSA specific T-cell responses were seen in the prostatectomized monkeys.

To investigate cell mediated responses to the administration of rV-PSA, lymphoproliferative assays were performed using PBMCs from animals receiving the recombinant vaccine. One of four monkeys receiving the lower dose of rV-PSA ($1 \times 10^7$ PFU) and four of four receiving the higher dose ($1 \times 10^8$ PFU) maintained specific T-cell responses to PSA protein up to 270 days following primary immunization as indicated by the lymphoproliferative assay (Table 5). Prostatectomy appeared to have no effect on either the humoral or cellular responses of monkeys receiving rV-PSA. Evidence of PSA specific T-cell responses in monkeys lacking mature antibody isotopes could be due to two distinct events following vaccination with rV-PSA: a T-cell independent event, leading to IgM production, and a T-cell dependent event, leading to specific lymphoproliferative responses.

TABLE 1

Inoculation protocol of rhesus monkeys with the PSA recombinant and wild-type vaccinia virus

| Monkey | Prostate | Immunogen | Dose* (PFU) |
|---|---|---|---|
| 1 | Yes | V-Wyeth | $1 \times 10^8$ |
| 2 | Yes | V-Wyeth | $1 \times 10^8$ |
| 3 | Yes | V-Wyeth | $1 \times 10^8$ |
| 4 | No | V-Wyeth | $1 \times 10^8$ |
| 5 | Yes | rV-PSA | $1 \times 10^7$ |
| 6 | Yes | rV-PSA | $1 \times 10^7$ |
| 7 | Yes | rV-PSA | $1 \times 10^7$ |
| 8 | No | rV-PSA | $1 \times 10^7$ |
| 9 | Yes | rV-PSA | $1 \times 10^8$ |
| 10 | Yes | rV-PSA | $1 \times 10^8$ |
| 11 | Yes | rV-PSA | $1 \times 10^8$ |
| 12 | No | rV-PSA | $1 \times 10^8$ |

*All animals received 3 immunizations at 4 week intervals.

TABLE 2

Mean WBC count, hematocrit, and differential count in rhesus monkeys receiving recombinant or wild-type vaccine

| | | V-Wyeth (n = 4) | | rV-PSA (n = 8) | |
|---|---|---|---|---|---|
| Test | Normal ranges | Before immunization[a] | After immunization[b] | Before immunization | After immunization |
| WBC | $7-15 \times 10^3$ | $5.0 \pm 0.8$ | $5.1 \pm 0.5$ | $5.2 \pm 0.7$ | $5.8 \pm 0.9$ |
| Hematocrit (vol. %) | 33-43 | $37.4 \pm 0.2$ | $37.0 \pm 0.1$ | $37.8 \pm 0.4$ | $37.0 \pm 0.5$ |
| Lymphocytes | $1-7 \times 10^3$ | $2.8 \pm 0.7$ | $3.9 \pm 0.5$ | $2.2 \pm 0.4$ | $3.5 \pm 0.8$ |
| SEGS[c] (%) | 3-69 | $2.0 \pm 0.2$ | $0.78 \pm 0.2$ | $2.9 \pm 0.6$ | $1.9 \pm 0.3$ |

TABLE 2-continued

Mean WBC count, hematocrit, and differential count in rhesus monkeys receiving recombinant or wild-type vaccine

| Test | Normal ranges | V-Wyeth (n = 4) | | rV-PSA (n = 8) | |
|---|---|---|---|---|---|
| | | Before immunization[a] | After immunization[b] | Before immunization | After immunization |
| Monocytes (%) | 0-8 | 0.1 ± 0.05 | 0.2 ± 0.04 | 0.1 ± 0.04 | 0.2 ± 0.50 |
| Eosinophils (%) | 0-8 | 0.1 ± 0.02 | 0.2 ± 0.10 | 0.1 ± 0.03 | 0.1 ± 0.02 |

[a]1 week prior to primary immunization
[b]12 weeks following primary immunization
[c]Segmented lymphocytes

TABLE 3

Mean serum chemistry values in rhesus monkeys receiving recombinant or wild-type vaccine

| Test | Normal ranges | V-Wyeth (n = 4) | | rV-PSA (n = 8) | |
|---|---|---|---|---|---|
| | | Before immunization[a] | After immunization[b] | Before immunization | After immunization |
| ALKP[c] (u/l) | 200-800 | 451 ± 48 | 610 ± 33 | 339 ± 74 | 454 ± 47 |
| BUN[d] (mg/dl) | 12-30 | 19.0 ± 3.0 | 17.8 ± 0.9 | 17.1 ± 0.6 | 20.5 ± 1.0 |
| ALT[e] (u/l) | 20-60 | 25.2 ± 1.9 | 22.8 ± 1.0 | 28.9 ± 5.3 | 25.8 ± 1.6 |
| AST[f] (u/l) | 40-80 | 37.8 ± 2.3 | 31.8 ± 4.4 | 37.9 ± 3.6 | 31.9 ± 2.4 |
| LDH[g] (u/l) | 200-500 | 194 ± 20 | 212 ± 21 | 236 ± 41 | 194 ± 13 |
| Creatine (mg/dl) | 0.5-1.0 | 0.9 ± 0.10 | 0.8 ± 0.03 | 0.8 ± 0.05 | 0.8 ± 0.02 |
| Creatine Kinase (u/l) | 500-2000 | 662 ± 112 | 466 ± 119 | 498 ± 120 | 563 ± 81 |

[a]1 week prior to primary immunization
[b]12 weeks following primary immunization
[c]Alkaline phosphatase
[d]Blood urea nitrogen
[e]Alanine aminotransferase
[f]Aspartate aminotransferase
[g]Lactate dehydrogenase

TABLE 4

Primate IgM[a] Response to Inoculation with rV-PSA

| Monkey | Immunogen | Dose (PFU) | PI[d] | 15 | 29[e] | 43 | 57[e] | 71 | 270 |
|---|---|---|---|---|---|---|---|---|---|
| 1 | V-Wyeth | 1 × 10⁸ | ND[f] | ND | ND | ND | ND | ND | ND |
| 2 | V-Wyeth | 1 × 10⁸ | ND | ND | ND | ND | ND | ND | ND |
| 3 | V-Wyeth | 1 × 10⁸ | ND | ND | ND | ND | ND | ND | ND |
| 4[c] | V-Wyeth | 1 × 10⁸ | ND | ND | ND | ND | ND | ND | ND |
| 5 | rV-PSA | 1 × 10⁷ | ND | >40 | 5 | 20 | >40 | >40 | ND |
| 6 | rV-PSA | 1 × 10⁷ | ND | >40 | ND | ND | 20 | 20 | ND |
| 7 | rV-PSA | 1 × 10⁷ | ND | >40 | 5 | 20 | 20 | 20 | ND |
| 8[c] | rV-PSA | 1 × 10⁷ | ND | >40 | 5 | 10 | >40 | >40 | ND |
| 9 | rV-PSA | 1 × 10⁸ | ND | 20 | 5 | 20 | 10 | 10 | ND |
| 10 | rV-PSA | 1 × 10⁸ | ND | 20 | 5 | 40 | >40 | NT[g] | ND |
| 11 | rV-PSA | 1 × 10⁸ | ND | >40 | >40 | >40 | >40 | >40 | ND |
| 12[c] | rV-PSA | 1 × 10⁸ | ND | >40 | 20 | 40 | 20 | 20 | ND |

[a]All monkey seras were negative for IgG to PSA at all time points; All seras were positive for IgG to vaccinia virus (>1:2000) at day 71.
[b]Monkeys received vaccinations on days 1, 29, and 57. Sera (1:5) was tested by ELISA. Titers were calculated using an O.D. of 0.4.
[c]Animal was prostatectomized.
[d]PI, Pre-immune.
[e]Animals bled before boosting.
[f]ND, not detectable; limit of detection was <1:5 dilution.
[g]NT, not tested.

TABLE 5

PSA Specific Lymphoproliferative T-cell Responses of Rhesus PBMCs 270 Days Following Inoculation with rV-PSA

| Monkey | Immunogen | Dose (PFU) | Antigen[a] | | | | |
|---|---|---|---|---|---|---|---|
| | | | Medium | Con A | Oval | UV-Wyeth | PSA[d] |
| 1 | V-Wyeth | $1 \times 10^8$ | 397 | 65701 | 376 | 24785 | 414 |
| 2[b] | V-Wyeth | $1 \times 10^8$ | NT | NT | NT | NT | NT |
| 3 | V-Wyeth | $1 \times 10^8$ | 450 | 84860 | 522 | 18859 | 413 |
| 4[c] | V-Wyeth | $1 \times 10^8$ | 532 | 107840 | 553 | 16571 | 387 |
| 5 | rV-PSA | $1 \times 10^7$ | 412 | 85276 | 408 | 6040 | 539 |
| 6 | rV-PSA | $1 \times 10^7$ | 401 | 96398 | 404 | 7776 | 3,134 |
| 7 | rV-PSA | $1 \times 10^7$ | 417 | 90801 | 522 | 10908 | 434 |
| 8[c] | rV-PSA | $1 \times 10^7$ | 1069 | 99216 | 744 | 15346 | 484 |
| 9 | rV-PSA | $1 \times 10^8$ | 384 | 106248 | 386 | 14499 | 10,635 |
| 10 | rV-PSA | $1 \times 10^8$ | 432 | 92263 | 404 | 19872 | 18,561 |
| 11 | rV-PSA | $1 \times 10^8$ | 411 | 94055 | 1063 | 5124 | 16,245 |
| 12[c] | rV-PSA | $1 \times 10^8$ | 420 | 124896 | 392 | 11944 | 12,945 |

[a]Antigen concentrations were: Con a (2 µg/ml); Ovalbumin (100 µg/ml); UV-Wyeth ($2 \times 10^7$ pfu/ml); and PSA (100 µg/ml). Each value represents a mean CPM of triplicate samples. Standard deviation never exceeded 10%.
[b]NT, Not Tested. B-cells were not transformed for this animal.
[c]Animal was prostatectomized.
[d]Values in bold are significant when compared to their respective medium control values (p < 0.001).

EXAMPLE II

Identification of Potential Prostate Specific Antigen (PSA) Specific T Cell Epitopes Since the entire amino acid sequence of human PSA is known and human class 1 HLA A2 consensus motifs have been described, studies were undertaken to identify a series of peptides that would potentially bind class 1 A2 molecules. A2 was chosen since it is the most common HLA class 1 molecule being represented in approximately 50% of North American Caucasians and 34% of African Americans. The peptide sequence of PSA was thus examined for matches to the consensus motifs for HLA A2 binding peptides. Peptides were only selected if their sequence diverged sufficiently from the PSA-related human glandular kallikrein (HGK) gene and pancreatic kallikrein antigen (PKA) sequences.

The amino acid sequence of human PSA was scanned using a predictive algorithm that combines a search for anchor residues with numerical assignments to all residues at all positions. The T2 cell binding assay was then used to determine which peptides bound human HLA A2 molecules. As can be seen in Table 6, PSA peptides 141-150, 154-163 and 146-154 scored positive in this assay (Nijman, H. W., et al., *Eur. J. Immunol.* 23:1215-1219, 1993). Table 7 gives the amino acid sequence of these peptides and compares them to corresponding sequences of HGK and PKA.

TABLE 6

PSA peptide binding assay

| Antigen | MAb A2, 69 |
|---|---|
| None | 127.25[a] |
| PSA 141-150 | 230.34 |
| PSA 146-154 | 223.97 |
| PSA 154-163 | 182.30 |

Peptides were used at a concentration of 50 µg/ml
[a]Mean channel fluorescent intensity.
CIRA2 cell line was used as positive control for anti-A2 staining [99.4 (241.15)].

TABLE 7

PSA peptide amino acid sequence

| PSA | 141-150 | F | L | T | P | K | K | L | Q | C | V |
|---|---|---|---|---|---|---|---|---|---|---|---|
| HGK | | — | — | R | — | R | S | — | — | — | — |
| PKA | | — | — | S | F | — | D | D | — | — | — |
| PSA | 146-154 | K | L | Q | C | V | D | L | H | V | |
| HGK | | S | — | — | — | — | S | — | — | L | |
| PKA | | D | — | — | — | — | — | — | K | I | |
| PSA | 154-163 | V | I | S | N | D | V | C | A | Q | V |
| HGK | | L | L | — | — | — | M | — | — | R | A |
| PKA | | I | L | P | — | — | E | — | E | K | A |

EXAMPLE III

Establishment of Human T Cell Lines

Cytolytic for Human Tumor Cells Expressing PSA

PBMC from normal healthy donors expressing the HLA A2 class 1 allele were used in an attempt to determine if PSA specific peptides are immunogenic for humans. Peptides 141-150 and 154-163 were used in this study. The methodology used for the establishment of these cell lines involves pulsing of PBMC with peptide and IL-2 as previously described (Tsang, K. Y., et al. *JNCI*, in press and in U.S. application Ser. No. 08/396,385, the disclosure of which is herein incorporated by reference). T cell lines were able to be established from 5/6 normal donors using PSA peptide 141-150 and from 6/6 normal donors using PSA peptide 154-163. Moreover, PBMC were obtained from two prostate cancer patients. T cell lines were established from these PBMC cultures using peptide 154-163.

Some of these T cell lines have been phenotyped. As seen in Table 8, one cell line designated T-866, which was derived from pulsing with peptide 141-150, contains appreciable amounts of CD4+/CD8+ double positive cells and another cell line, designated T-1538, derived from pulsing with peptide 154-163, shows a similar phenotype.

Four of the T cell lines derived from three different individuals were then assayed for their ability to lyse human cells (Table 9). As seen in Table 9, the T cell line designated T-866, derived from peptide 141-150, was able to lyse T2 cells when pulsed with the appropriate peptide (141-150). No lysis was seen using the PSA negative human colon cancer cell line COLO-205. While 80% lysis was seen using the LNCAP PSA containing human prostate cancer cell line. When employing the NK target K562, which measures non-specific lysis due to NK cell activity, only 23% lysis was obtained. Similar results were seen employing a different T cell line obtained from the same patient which was derived from pulsing with PSA peptide 154-163. Two additional T cell lines which were derived from peptide 154-163 were also analyzed. One was from a normal donor (T-1538) and one was from a prostate cancer patient (T-PC2). As can be seen in Table 9, employing both of these T cell lines, enhanced lysis was seen when the T2 cell line was pulsed with the 154-163 peptide and enhanced lysis was seen when employing the PSA expressing prostate specific cell line LNCAP, as compared to COLO-205 or K562. These studies demonstrate that T cell lines can be established using the peptides and protocols generated here which have the ability to lyse PSA expressing human prostate carcinoma cells.

TABLE 8

Flow cytometry analysis of PSA peptide specific T cells

| T-cell Line | PSA Peptide | CD3 | CD4 | CD8 | CD4/CD8 | CD56 |
|---|---|---|---|---|---|---|
| T-866 | 141-150 | 96 | 35 | 6.5 | 59 | 0 |
| T-1538 | 154-163 | 94 | 5.2 | 32 | 62 | 0 |

TABLE 9

Cytotoxic effects of PSA peptide specific T cells

| T-cell Line | PSA Peptide | % specific release (lysis) | | | | |
|---|---|---|---|---|---|---|
| | | T2 | T2 + peptide | LNCAP | K562 | COLO-205 |
| T-866 | 141-150 | 10[a] | 40 | 80 | 23 | 7 |
| T-866 | 154-160 | 16 | 35 | 60 | 22 | 10 |
| T-1538 | 154-160 | 10 | 40 | 29 | 3 | 10 |
| T-PC2 | 154-160 | 15 | 35 | 35 | 2 | 8 |

[a]percent of $^{111}$In specific release
24 hour cytotoxic assay (E:T ratio, 25:1) (SD < 2.5%)

The following is a listing of publications referred to in the foregoing specification.

Armbruster, D. A. Prostate-specific antigen: biochemistry, analytical methods, and clinical application. *Clinical Chemistry,* 39:181-195, (1993).

Bilhartz, D. L., Tindall, D. J., and Oesterling, J. E. Prostate-specific antigen and prostatic acid phosphatase: biomolecular and physiological characteristics. *Urology,* 38:95-102, (1991).

Brawer, M. K., and Lange, P. H. Prostate-specific antigen and premalignant change: implications for early detection. *CA Cancer Journal Clinic,* 39:361-375, (1989).

Carter, H. B., and Coffey, D. S. The prostate: an increasing medical problem. *Prostate,* 16:39-48, (1990).

Chatterjee, M. B., Foon, K. A., and Kohler, H. Idiotypic antibody immunotherapy of cancer. *Cancer Immunology and Immunotherapy,* 38:75-82, (1994).

Cheever, M. A., Chen, W., Disis, M. T., and Peace, D. J. T-cell immunity to oncogenic proteins including mutated RAS and chimeric BCR-ABL. *Annals of the New York Academy of Science,* 690:101-112, (1993).

Choe, B. K., Frost, P., Morrison, M. K., and Rose, N R. Natural killer cell activity of prostatic cancer patients. *Cancer Investigations,* 5:285-291, (1987).

Conry, R. M., Salch, M. N., Schlom, J., and LoBuglio, A. F. Breaking tolerance to carcinoembryonic antigen with a recombinant vaccinia virus vaccine in man. *American Association of Cancer Research* (Abstract), (1994).

Correale, P., Zaremba, S., Nieroda, C., Zhu, M. Z., Schmitz, J., Schlom, J., and Tsang, K. Y. In vitro stimulation of human cytotoxic T lymphocytes specific for peptides derived from prostate specific antigen. *9th International Congress of Immunology* (Abstract), (1995).

Disis, M. L., Smith, J. W., Murphy, A. A., Chen, W., and Cheever, M. A. In vitro generation of human cytolytic T-cells specific for peptides from the HER-2/neu protooncogene protein. *Cancer Research,* 54:1071-1076, (1994).

Donovan, J. F., Lubaroff, D. M., and Williams, R. D. Immunotherapy of prostate cancer. *Problems in Urology,* 4:489-505, (1990).

Foon, K. A., Chakraborty, M., John, W., Sherratt, A., Kohler, H., and Bhattacharya-Chatterjee, M. Active immunity to the carcinoembryonic antigen (CEA) in patients treated with an anti-idiotype monoclonal antibody vaccine. *Society for Biological Therapy* (Abstract), (1994).

Gauthier, E. R., Chapdelaine, P., Tremblay, R. R., and Dube, J. Y. Characterization of rhesus monkey prostate specific antigen cDNA. *Biochimica Biophysica Acta,* 1174:207-210, (1993).

Gritz, L., Destree, A., Cormier, N., Day, E., Stallard, V., Caiazzo, T., Mazzara, G., and Panicali, D. Generation of hybrid genes and proteins by vaccinia virus-mediated recombination: application to human immunodeficiency virus type 1 env. *J. Virol.* 64:5948-5957, (1990).

Helling, F., and Livingston, P. O. Ganglioside conjugate vaccines. Immunotherapy against tumors of neuroectodermal origen. *Molecular and Chemical Neuropathology,* 21:299-309, (1994).

Helling, F., Calves, M., Shang, Y., Oettgen, H. F., and Livingston, P. O. Construction of immunogenic GD3-conjugate vaccines. *Annals of the New York Academy of Science,* 690:396-397, (1993).

Huang, C, L., Brassil, D., Rozzell, M., Schellhammer, P. F., and Wright, G. L. Comparison of prostate secretory protein with prostate specific antigen and prostatic acid phosphatase as a serum biomarker for diagnosis and monitoring patients with prostate carcinoma. *Prostate,* 23:201-212, (1993).

Ioannides, C. G., Fisk, B., Fan, D., Biddison, W. E., Wharton, J. T., and O'Brian, C. Cytotoxic T cells isolated from ovarian malignant ascites recognize a peptide derived from the HER-2/neu proto-oncogene. *Cellular Immunology,* 151:225-234, (1993).

Irvine, K., Kantor, J., and Schlom, J. Comparison of a CEA-recombinant vaccinia virus, purified CEA, and an anti-idiotype antibody bearing the image of a CEA epitope in the treatment and prevention of CEA-expressing tumors. *Vaccine Research,* 2:79-94, (1993).

Isaacs, J. T., Feitz, W. F., and Scheres, J. Establishment and characterization of seven Dunning rat prostatic cancer cell lines and their use in developing methods for predicting metastatic abilities of prostatic cancers. *Prostate,* 9:261-281, (1986).

Jenkins, S., Gritz, L., Fedor, C., O'Neil, E., Cohen, L. and Panicali, D. Formation of lentivirus particles in mammalian cells infected with recombinant fowlpox virus. *AIDS Research and Human Retroviruses* 7:991-998, (1991).

Kantor, J., Irvine, K., Abrams, S., Kaufman, H., Dipietro, J., and Schlom, J. Antitumor activity and immune responses induced by a recombinant carcinoembryonic antigen-vaccinia virus vaccine. *Journal of the National Cancer Institute,* 84:1084-1091, (1992a).

Kantor, J., Irvine, K., Abrams, S., Snoy, P., Olsen, R., Greiner, J., Kaufman, H., Eggensperger, D., and Shlom, J. Immunogenicity and safety of a recombinant vaccinia virus vaccine expressing the carcinoembryonic antigen gene in a nonhuman primate. *Cancer Research,* 52:6917-6925, (1992b).

Karr, J. F., Kantor, J. A., Hand, P. H., Eggensperger, D. L., and Schlom, J. Conservation of the prostate specific antigen (PSA) gene in primates and the expression of recombinant human PSA in a transfected murine cell line. *Cancer Research*: Submitted for Publication, (1995).

Kaufman, H., Schlom, J., and Kantor, J. A recombinant vaccinia virus expressing human carcinoembryonic antigen (CEA). *International Journal of Cancer,* 48:900-907, (1991).

Kleer, E., and Oesterling, J. E. PSA and staging of localized prostate cancer. *Urologic Clinics of North America,* 20:695-704, (1993).

Lilja, H. Structure, function, and regulation of the enzyme activity of prostate-specific antigen. *World Journal of Urology,* 11:188-191, (1993).

Livingston, P. O., Calves, M. J., Helling, F., Zollinger, W. D., Blake, M. S., and Lowell, G. H. GD3/proteosome vaccines induce consistent IgM antibodies against the ganglioside GD3. *Vaccine,* 12:1199-1204, (1993).

Lundwall, A., and Lilja, H. Molecular cloning of human prostate specific antigen cDNA. *FEBS Letters,* 214:317-322, (1987).

McEntee, M., Isaacs, W., and Smith, C. Adenocarcinoma of the canine prostate: immunohistochemical examination for secretory antigens. *Prostate,* 11:163-170, (1987).

Moss, B. Generation of recombinant vaccinia viruses. *Current Protocols in Molecular Biology,* 2:16.15.1-16.18.9, (1993).

Oesterling, J. E. Prostate specific antigen: a critical assessment of the most useful tumor marker for adenocarcinoma of the prostate. *Journal of Urology,* 145:907-923, (1991).

Panicali, D., Grzelecki, A. and Huang, C. Vaccinia virus vectors utilizing the β-galactosidase assay for rapid selection of recombinant viruses and measurement of gene expression. *Gene* 47:193-199, (1986).

Paoletti, E., Tartaglia, J., and Cox, W. I. Immunotherapeutic stratagies for cancer using poxvirus vectors. *Annals of the New York Academy of Sciences,* 690:292-300, (1993).

Peace, D. J., Xue, B., Sosman, J. A., and Zhang, Y. In vitro immunization of human cytotoxic T lymphocytes specific for peptides derived from prostate specific antigen. *Cancer Vaccines: Structural Basis for Vaccine Development* (Abstract), (1994).

Powrie, F., and Coffman, R. L. Cytokine regulation of T-cell function: potential for therapeutic intervention. *Immunology Today,* 14:270-274, (1993).

Ravindranath, M. H., Brazeau, S. M., and Morton, D. L. Efficacy of tumor cell vaccine after incorporating monophosphoryl A (MPL) in tumor cell membranes containing tumor associated ganglioside. *Experimentia,* 50:648-653, (1994).

Ritter, G., Boosfeld, E., Adluri, R., Calves, M., Oettgen, H. F., Old, L. J., and Livingston, P. Antibody response to immunization with ganglioside GD3 and GD3 congeners (lactones, amide, and ganglisidol) in patients with malignant melanoma. *International Journal of Cancer,* 48:379-385, (1991).

Schellhammer, P. F., and Wright, G. L. Biomolecular and clinical characteristics of PSA and other candidate prostate tumor markers. *Urologic Clinics of North America,* 20:597-606, (1993).

Schlom, J., Kantor, J., Abrams, S., Tsang, K. Y., Panicali, D., and Hamilton, J. M. Strategies for the development of recombinant vaccines for the immunotherapy of breast cancer. *Breast Cancer Research and Treatment,* In Press.

Schroder, F. H. Experimental Models in the study of prostate cancer. Prostate Cancer. In: *International Perspectives in Urology.,* 3:343-377, (1982).

Tsang, K. Y., Nieroda, C. A., De Filippi, R., Chung, Y. K., Yamaue, H., Greiner, J. W., and Schlom, J. Induction of human cytotoxic T cell lines directed against point-mutated p21 Ras-derived synthetic peptides. *Vaccine Research,* 3:183-193, (1994).

Wakui, S., Furusato, M., Nomura, Y., Asari, M., and Kano, Y. Lectin histochemical study of the prostate gland of the rhesus monkey (Macaca mulatta). *Journal of Anatomy,* 181:127-131, (1992).

Wang, M. C., Kuriyama, M., Papsidero, L. D., Loor, R. M., Valenzuela, L. A., Murphy, G. P., and Chu, T. M. Prostate antigen of human cancer patients. *Methods in Cancer Research,* 19:179-197, (1982).

Wang, M. C., Valenzuela, L. A., Murphy, G. P., and Chu, T. M. Purification of a human prostate specific antigen. *Investigations in Urology,* 17:159-163, (1979).

Zietman, A. L., Shipley, W. L., and Willett, C. G. Residual disease after radical surgery or radiation therapy for prostate cancer. Clinical significance and therapeutic implications. *Cancer,* 71:959-969, (1993).

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

What is claimed is:

1. A method for generating a cytotoxic T-cell eliciting immune response to prostate-specific antigen (PSA) in a human host, comprising administering to the host a first pox virus vector to stimulate an immune response, wherein the first pox virus vector has at least one insertion site containing a DNA segment encoding PSA or a cytotoxic T-cell eliciting epitope thereof operably linked to a promoter such that the DNA segment is expressed to produce PSA or the cytotoxic T-cell eliciting epitope thereof in the host in a sufficient amount to generate a cytotoxic T-cell eliciting immune response, and then administering an additional PSA or T-cell eliciting epitope thereof in a manner selected from the group consisting of in a second pox virus vector, in a formulation with an adjuvant, with a cytokine, with a co-stimulatory molecule, in a liposomal formulation, and a combination thereof.

2. The method of claim 1, wherein the pox virus vector is selected from the group of pox viruses consisting of suipox, avipox, and capripox virus.

3. The method of claim 2, wherein the avipox is fowlpox, canary pox or pigeon pox.

4. The method of claim 1, wherein the adjuvant is selected from the group consisting of RIBI Detox, QS21 and incomplete Freund's adjuvant.

5. The method of claim 1, wherein the cytokine is selected from the group consisting of IL-2, IL-6, or IL-12.

6. The method of claim 1, wherein the costimulatory molecule is selected from the group consisting of B7.1 or B7.2.

7. The method of claim 1, further comprising administering to the host additional cytokine or co-stimulatory molecule.

8. The method of claim 1 or 7, wherein the cytokine or co-stimulatory molecule is administered in a manner selected from the group consisting essentially the first pox virus, the second pox virus, systemically, and combinations thereof.

9. The method of claim 1, wherein the method comprises administering additional PSA or a cytotoxic T-cell eliciting epitope thereof in a second pox virus, and the second pox virus vector is from a genus other than the first pox virus vector.

10. The method of claim 9, wherein the first pox virus is selected from the group of pox viruses consisting of suipox, avipox, capripox, and orthopox.

11. The method of claim 9, wherein the first pox virus vector is vaccinia and the second pox virus vector is avipox.

12. The method of claim 11, wherein the avipox is fowlpox.

13. The method of claim 1, the second administration is about 1 month to about 3 months after the first administration.

14. The method of claim 13, wherein the second administration is about one month after the first administration.

15. The method of claim 13, wherein the second administration is about 2 months after the first administration.

16. The method of claim 13, wherein the second administration is about 3 months after the first administration.

17. The method of claim 1, wherein the first pox virus vector is administered via a route selected from the group consisting of intradermal, subcutaneous, intramuscular, intravenous, and intraperitoneal administration.

18. The method of claim 1, wherein the second pox virus vector is administered via a route selected from the group consisting of intradermal, subcutaneous, intramuscular, intravenous, and intraperitoneal administration.

* * * * *

UNITED STATES PATENT AND TRADEMARK OFFICE
CERTIFICATE OF CORRECTION

PATENT NO. : 7,598,225 B1  Page 1 of 1
APPLICATION NO. : 09/693121
DATED : October 6, 2009
INVENTOR(S) : Schlom et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 436 days.

Signed and Sealed this

Fourteenth Day of December, 2010

David J. Kappos
*Director of the United States Patent and Trademark Office*